US00RE35517E

United States Patent [19]

Gee et al.

[11] E Patent Number: Re. 35,517

[45] Reissued Date of Patent: May 20, 1997

[54] METHOD, COMPOSITIONS, AND COMPOUNDS FOR MODULATING BRAIN EXCITABILITY

[75] Inventors: Kelvin W. Gee, Irvine; Michael B. Bolger, Los Alamitos; Nancy C. Lan, South Pasadena, all of Calif.

[73] Assignee: University of Southern California, Los Angeles, Calif.

[21] Appl. No.: 980,377

[22] Filed: Nov. 23, 1992

Related U.S. Patent Documents

Reissue of:

[64] Patent No.: 5,120,723
Issued: Jun. 9, 1992
Appl. No.: 521,724
Filed: May 10, 1990

U.S. Applications:

[63] Continuation-in-part of Ser. No. 379,047, Jul. 13, 1989, abandoned, which is a continuation-in-part of Ser. No. 89,362, Aug. 25, 1987, abandoned.

[51] Int. Cl.[6] ..... A61K 31/56; A61K 31/44; A61K 31/425; A61K 31/445; A61K 31/58; A61K 31/495; C07J 41/00; C07J 7/00

[52] U.S. Cl. ..... 514/176; 514/177; 514/178; 514/179; 514/180; 514/181; 514/182; 540/89; 540/94; 540/95; 540/97; 540/99; 540/106; 540/107; 540/108; 540/109; 540/110; 540/111; 540/112; 540/113; 540/114; 540/118; 540/119; 540/120; 552/505; 552/540; 552/541; 552/542; 552/544; 552/546; 552/547; 552/612; 548/146; 548/201

[58] Field of Search ..... 514/176–182

[56] References Cited

U.S. PATENT DOCUMENTS

| | | | |
|---|---|---|---|
| 2,797,230 | 6/1957 | Nicholls | 260/397.45 |
| 2,861,089 | 11/1958 | Graham | 260/397.45 |
| 3,197,470 | 7/1965 | Deghenghi et al. | 260/239.55 |
| 4,213,978 | 7/1980 | Bodor et al. | 424/241 |

FOREIGN PATENT DOCUMENTS

| | | |
|---|---|---|
| 0030368 | 6/1981 | European Pat. Off. . |
| 927030 | 4/1955 | Germany . |
| 2218413 | 11/1972 | Germany . |
| 744237 | 5/1952 | United Kingdom . |

OTHER PUBLICATIONS

Beard et al., "The Methylenation of Unsaturated Ketones," *Tetrahedron* 25:1219–1239 (1969).

Besch et al., "A Review of Some Aspects of the Metabolism of Progestational Agents," *Metabolism* 14(3), Part 2:432–443 (1965).

Chemical Abstracts 52, Abstract for German Patent Appl. No. 927,030, Rosenkranz et al., "Allopregnane–17α, 21–diol,3,11,20–trione and Its Esters" (1958.

Aird, R.B., and Gordon, G.S., "Anticonvulsive Properties of Desoxycorticosterone," J. Am. Med. Assoc. 145(10):715–719 (1951).

Backstrom, T., Bixo, M., and Hammarback, S., "Ovarian steroid hormones: Effects on mood, behaviour, and brain excitability," Acta. Obstet. Gynecol. Scand. Suppl. 130:19–24 (1985).

Barker, J.L., Harrison, N.L., Lange, G.D., and Owen, D.G., "Potentiation of GABA activated chloride conductance by a steroid anaesthetic in cultured rat spinal neurones," J. Physiol. 386:485–501 (1987).

Barnes, D.M., "Steroids may influence changes in mood," Science 23:1344–1345 (Jun., 1986).

Callachan, H., Cotrell, G.A., Hather, N.Y., Lambert, J.J., Nooney, J.M., and Peters, J.A., "Modulation of the $GABA_a$ receptor by progesterone metabolites" (1987).

Craig, C.R. (G.D. Searle), "Anticonvulsive activity of steroids: Separability of anticonvulsant from hormonal effects," J. Pharm. Exper. Ther. 153(2):337–343 (1966).

Crawley, J.N., Glowa, J.R., Majewska, M.D., and Paul, S.M., "Anxiolytic activity of an endogenous adrenal steroid," Brain Research 398:382–395 (1986).

Gee, K.W., Chang, W.C., Brinton, R.E., and McEwen, B.S., "GABA–dependent modulation of the $Cl^-$ ionophore by steroids in rat brain," Eur. J. Pharmacol. 136:419–423 (1987).

Gyermek, L., Iriarte, J., and Grabbe, P., "Steroids. CCCX. Structure–Activity Relationship of Some Steroidal Hypnotic Agents," J. Med. Chem. 11:117–125 (1968).

Harrison, N.L., Majewska, M.D., Harrington, J.W., and Barker, J.L., "Structure–activity relationships for steroid interaction with the γ–Aminobutyric acid receptor complex," J. Pharm. Exper. Ther. 241(1):346–353 (1987).

Hewett, C.L., Savage, D.S., Lewis, J.J., and Sugrue, M.J. (Organon labs Ltd.), "Anticonvulsant and interneuronal blocking activity in some synthetic aminosteroids," J. Pharm. Lond. 16:765–767 (1964).

Hogskilde, S., Wagner, J., Carl., P., Anker, N., Angelo, H.R., and Sorensen, M.B., "Anticonvulsive properties of pregnanolone emulsion compared with Althesin and thiopentone in mice," Br. J. Anaesth. 16:462–467 (1988).

Lambert, J.J., Peters, J.A., and Cottrell, G.A., "Actions of synthetic and endogenous steroids on the $GABA_A$ receptor," TIPS 8:224–227 (1987).

Landgren, S.L., Aasly, J., Backstrom, T., Dubrovsky, D., and Danielson, E., "The effect of progesterone and its metabolites on the interictal epileptiform discharge in the cat's cerebral cortex," Acta. Physiol. Scand. 131:33–42 (1987).

Majewska, M.D., "Steroids and Brain Activity: Essential dialogue between body and mind," Biochem. Pharmacol. 36(22):3781–3788 (1987).

(List continued on next page.)

*Primary Examiner*—Cecilia Tsang
*Attorney, Agent, or Firm*—Sterne, Kessler, Goldstein & Fox P.L.L.C.

[57] ABSTRACT

Method, compositions, and compounds for modulating brain excitability to alleviate stress, anxiety, and seizure activity using certain steroid derivatives that act at a newly identified site on the gamma-ammobutyric acid/benzodiazepine receptor-chloride ionpore (GBR) complex.

10 Claims, 5 Drawing Sheets

OTHER PUBLICATIONS

Majewska, M.D., Harrison, N.L., Schwartz, R.D., Barker, J.L., and Paul, S.M., "Steroid hormone metabolites are Barbiturate–Like modulators of the GABA receptor," Science 232:1004–1007 (1986).
Marshall, C.W., "5–Pregnen–3b–ol–20–one 3–aminoalkanoates," Belg. patent 621,470, Feb. 18, 1963, CA 59:12883.
Morrow, A.L., Suzdak, P.D., and Paul, S.M., "Steroid hormone metabolites potentiate GABA receptor–mediated chloride ion flux with nanomolar potency," Eur. J. Pharm. 142:483–485 (1987).
Munari, C., Casaroli, D., Matteuzzi, G., and Pacifico, L., "The use of Althesin in Drug–Resistant Status Epilepticus," Epilepsia 20:475–482 (1979).
Riu, P.L., Susini, G., and Ruju, P., "Anticonvulsant activity of Althesin on Experimental Epilepsy," Br. J. Anaesth. 54:343–347 (1982).
Roussel–UCLAF, "Antispasmodics," Fr. patent M1764, May 6, 1963, CA 59:12877.
Selye, H., "The antagonism between anesthetic steroid hormones and pentamethylenetetrazol (Metazol)," *J. of Lab. and Clin. Med.*, 27, 1051–1054 (1942).
Werboff, J., Hedlund, L., and Havlena, J., "Audiogenic seizures in Adult Male castrated Rats treated with various hormones," General and Comp. Endo. 3:389–397 (1963).
Woodbury, D.M., "Effect of Adrenocortical Steroids and Adrenocorticotrophic Hormone on Electroshock Seizure Treshold," J.P.E.T. 105:27–36 (1952).
Woodbury, D.M., "Effect of hormones on brain excitability and electrolytes," Recent Prog. Horm. Res. 10:65–107 (1954).
Arafat, E. et al., "Sedative and Hypnotic Effects Of Oral Administration Of Micronized Progesterone May Be Mediated Through Its Metabolites," Am J Obstet Gynecol 159:1203–1209 (1988).
Conney, A.H. et al., "Decreased Central Depressant Of Progesterone And Other Steroids In Rats Pretreated With Drugs and Insecticides," The Journal Of Pharmacology And Experimental Therapeutics 154:310–318 (1966).
Gyermek, L., "Pregnanolone: A Highly Potent, Naturally Occurring Hypnotic–Anesthetic Agent (32276)," Institute Of Hormone Biology Syntex Research, P.S.E.B.M. 125:1058–1062 (1967).
Gyermek, L. et al., "Some Effects Of Progesterone And Related Steroids On The Central Nervous System," Int. J. Neuropharmacol 6:191–198 (1967).
Mendelson, W.B. et al., "Sleep Induction By An Adrenal Steroid In The Rat," Pyschopharmacology 93:226–229 (1987).
Raisinghani, K.H. et al., "Uptake Of Intravenously Administered Progesterone, Pregnanedione And Pregnanolone By The Rat Brain," Acta Endocrinologica 57:395–404 (1968).
Nagata, CA 74: 13317 (1970).
Pfaff D. W. et al. Science, 219:808–814 (1983).
Laidlaw, Laucet, 1235–1237 (1956).
Marker, R.E. et al, J.A.C.S. 59, 616–618 (1937).
Bordor, Drugs of the Future, 6(3):165–182 (1981).
Morrian et al, Biochem. 40: 376–380 (1947).
Lawrence, L.J. et al, Biochem. Biophys. Res. Comm. 123: 1130–1137 (1984).
Backstrom, T. et al., Acta, Endocr. Supp. 256–257, 1983.
Bodor, J. Pharmaceutical Sciences, 73(3):385–389 (1984).
Dalton, K., The Premenstrual Syndrome and Progesterone Therapy, 2nd Edition, 1984.
Notari, R.E., Methods in Enzymology, 112:309–323 (1985).
Rosciszewska, D., et al., J. Neurol. Neurosurg. Psych. 49:47–51 (1986).
Squires, R.F. et al., Mol. Pharmacol., 23;326–336, 1983.
Swinyard, E.A. et al, Antiepileptic Drugs, D. M. Woodbury, J.K. Penry and C.E. Pippenger, eds., p. 111 (Raven Press, New York) 1982.
Wood, P.L., et al, J. Pharmacol. Exp. Ther. 231:572–576 (1984).
Worms, P. L. et al., J. Pharmacol. Exp. Ther. 220:660–671 (1982).
Dennerstein et al, British Medical Journal, 290:1617–1621, 1985.
Gee, K. W. et al., in Drugs In Central Nervous System Disorders, pp. 123–147, D.C. Horvell, ed. 1985.
Gee, K.W. et al., Molecular Pharmacology, 30:218–225, 1986.
Maddocks, S., et al., Obstet. Gynecol., 154:573–81, 1986.
Maksay, G. et al. J. Neurochem., 44:480–486, 1985.
Mattson, R.H. et al, in Advances in Epileptology, XVth Epilepsy Int. Symposium, 279–282, 1984.

FIG. 2A
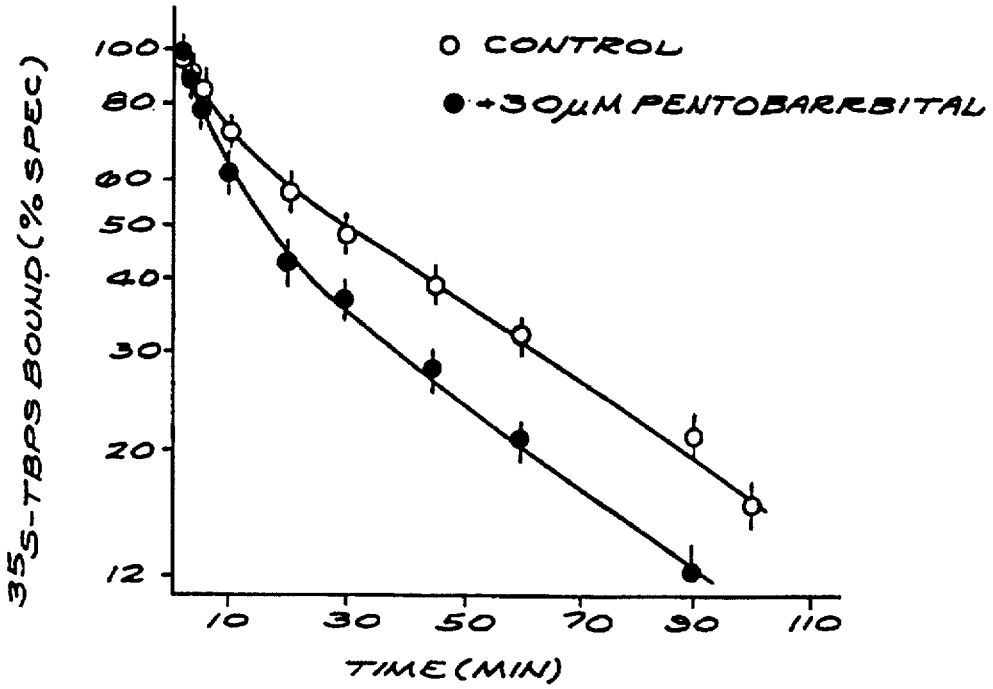
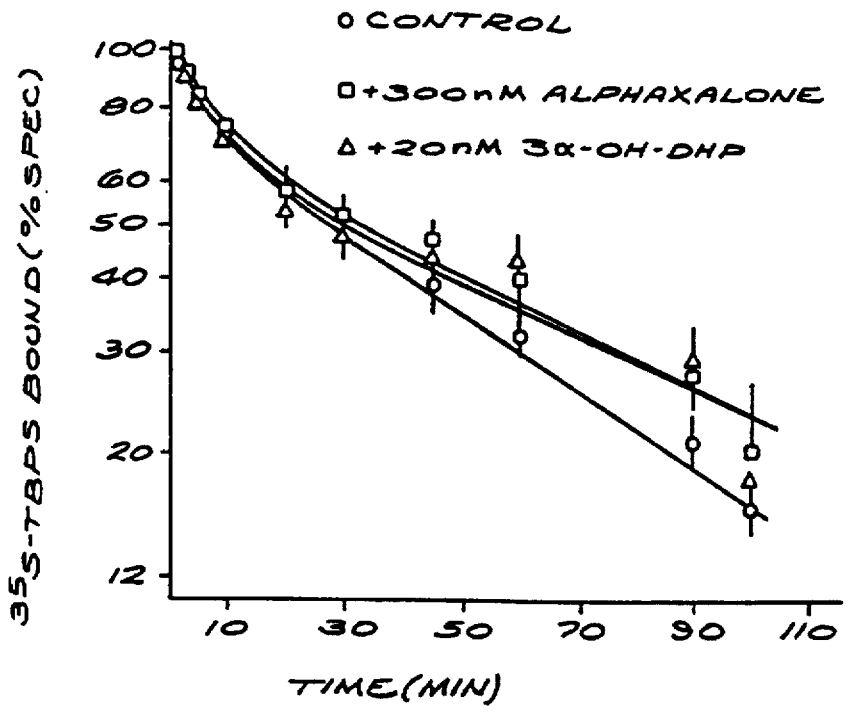
FIG. 2B

EFFECT OF PENTOBARBITAL ON 3 ALPHA-OH-DHP MODULATION OF [$^3$H] FLUNITRAZEPAM BINDING IN RAT HIPPOCAMPAL HOMOGENATES

METHOD, COMPOSITIONS, AND COMPOUNDS FOR MODULATING BRAIN EXCITABILITY

Matter enclosed in heavy brackets [ ] appears in the original patent but forms no part of this reissue specification; matter printed in italics indicates the additions made by reissue.

REFERENCE TO RELATED APPLICATION

This application is a continuation-in-part of copending application Ser. No. 379,047 filed Jul. 13, 1989, which in turn is a continuation-in-part of application Ser. No. 089,362 filed Aug. 25, 1987, both now abandoned.

BACKGROUND OF THE INVENTION

The present invention is directed to a method compositions, and compounds for modulating animal brain excitability via the gamma-aminobutyric acid (GABA)/benzodiazepine (BZ) receptor-chloride ionopore complex (GBR complex).

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −80 mv, the cell interior being negative with respect to the cell exterior. The potential (voltage) is the result of ion ($K^+$, $Na^+$, $Cl^-$, organic anions) balance across the neuronal semi-permeable membrane. Neurotransmitters are stored in presynaptic vesicles and are released under the influence of neuronal action potentials. When released into the synaptic cleft, an excitatory chemical transmitter such as acetylcholine will cause membrane depolarization (change of potential from −80 mv to −50 mv). This effect is mediated by post-synaptic nicotinic receptors which are stimulated by acetylcholine to increase membrane permeability to $Na^+$ ions. The reduced membrane potential stimulates neuronal excitability in the form of a post-synaptic action potential.

In the case of the GBR complex, the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GBR complex to facilitate the flow of chloride ions down a concentration gradient of the GBR complex into the cell. An intracellular increase in the levels of this anion causes hyperpolarization of the transmembrane potential, rendering the neuron less susceptible to excitatory inputs (i.e., reduced neuron excitability). In other words, the higher the chloride ion concentration, the lower the brain excitability (the level of arousal).

It is well-documented that the GBR complex is [responsible for] *involved in* the mediation of anxiety, seizure activity, and sedation. Thus, GABA and drugs that act like GABA or facilitate the effects of GABA (e.g., the therapeutically useful barbiturates and benzodiazepines (BZs) such as Valium) produce their therapeutically useful effects by interacting with specific regulatory sites on the GBR [receptor] complex.

It has also been observed that a series of steroid metabolites interact with the GBR receptor complex to alter brain excitability (Majewska, M. D. et al., "Steroid hormone metabolites are barbiturate-like modulators of the GABA receptor," Science, 232:1004–1007, 1986; Harrison, N. L. et al., Structure-activity relationships for steroid interaction with the gamma-aminobutyric acid-A receptor complex," J. Pharmacol. Exp. Ther., 241:346–353, 1987). [prior] *Prior* to the present invention, the therapeutic usefulness of these steroid metabolites was not recognized by workers in the field due to an incomplete understanding of the potency and site of action. Applicants' invention relates to a pharmaceutical application of the knowledge gained from a more developed understanding of the potency and site of action of certain steroid compounds.

The ovarian hormone progesterone and its metabolites have also been demonstrated to have profound effects on brain excitability (Backstrom, T. et al., "Ovarian steroid hormones: effects on mood, behaviour and brain excitability," Acta Obstet. Gynecol. Scand Suppl. 130:19–24, 1985; Pfaff, D. W. and McEwen, B. S., "Actions of estrogens and progestins on nerve cells," Science, 219:808–814, 1983; Gyermek, et al., 1968, "Structure-activity relationship of some steroidal hypnotic agents," J. Med. Chem. 11:117). The levels of progesterone and its metabolites vary with the phases of the menstrual cycle. It has been well-documented that progesterone and its metabolites decrease prior to the onset of menses. The monthly recurrence of certain physical symptoms associated with the onset of menses has also been well documented. These symptoms, which have become associated with premenstrual syndrome (PMS) include stress, anxiety, and migraine headaches (Dalton, K., Premenstrual Syndrome and Progesterone Therapy, 2nd edition, Chicago: Chicago Yearbook, 1984). Patients with PMS have a monthly recurrence of symptoms that are present in premenses and absent in postmenses.

In a similar fashion, a reduction in progesterone has also been temporally correlated with an increase in seizure frequency in female epileptics (i.e., catamenial epilepsy; Laidlaw, J., "Catamenial epilepsy," Lancet, 1235–1237, 1956). A more direct correlation has been observed with a reduction in progesterone metabolites (Roscizsewska et al., "Ovarian hormones, anticonvulsant drugs and seizures during the menstrual cycle in women with epilepsy," J. Neurol. Neurosurg. Psych., 49:47–51, 1986). In addition, for patients with primary generalized petit mal epilepsy, the temporal incidence of seizures has been correlated with the incidence of the symptoms of premenstrual syndrome (PMS) (Backstrom, T. et al., "Production of 5-alpha-pregnane-3, 20-dione by human corpus lutem," Acta Endrocr. Suppl. 256:257, 1983).

A syndrome also related to low progesterone levels is postnatal depression (PND). Immediately after birth progesterone levels decrease dramatically leading to the onset of PND. The symptoms of PND range from mild depression to psychosis requiring hospitalization; PND is associated with severe anxiety and irritability. PND-associated depression is not amendable to treatment by classic antidepressants and women experiencing PND show an increased incidence of PMS (Dalton, K., 1984, op. cit.).

Collectively, these observations imply a crucial role for progesterone in the homeostatic regulation of brain excitability, which is manifested as an increase in seizure activity or symptoms associated with catamenial epilepsy, PMS, and PND. The correlation between reduced levels of progesterone and the symptoms associated with PMS, PND, and catamenial epilepsy (Backstrom, et al., 1983, op. cit.; Dalton, K., 1984, op. cit.) has prompted the use of progesterone in their treatment (Mattson, et al., "Medroxyprogesterone therapy of catamenial epilepsy," in Advances in epileptology: XVth Epilepsy International Symposium, Raven Press, New York, 279–282, 1984, and Dalton, K., 1984, op. cit.). However, progesterone in not consistently effective in the treatment of the aforementioned syndromes. For example, no dose-response relationship exists for progesterone in the treatment of PMS (Maddocks, et al., "A double-blind placebo-controlled trial of progesterone vaginal suppositories in the treatment of premenstrual syndrome," J. Obstet. Gynecol. 154:573–581, 1986; Dennerstein, et al., British Medical Journal, 290:16–17, 1986).

BRIEF DESCRIPTION OF THE DRAWINGS

The present invention may be better understood and its advantages appreciated by those skilled in the art by referring to the accompanying drawings wherein

FIGS. 2A and 2B are plots of the binding percentage of [$^{35}$S] t-butylbicyclophosphorothionate vs. time;

SUMMARY OF THE INVENTION

Figure 1A:
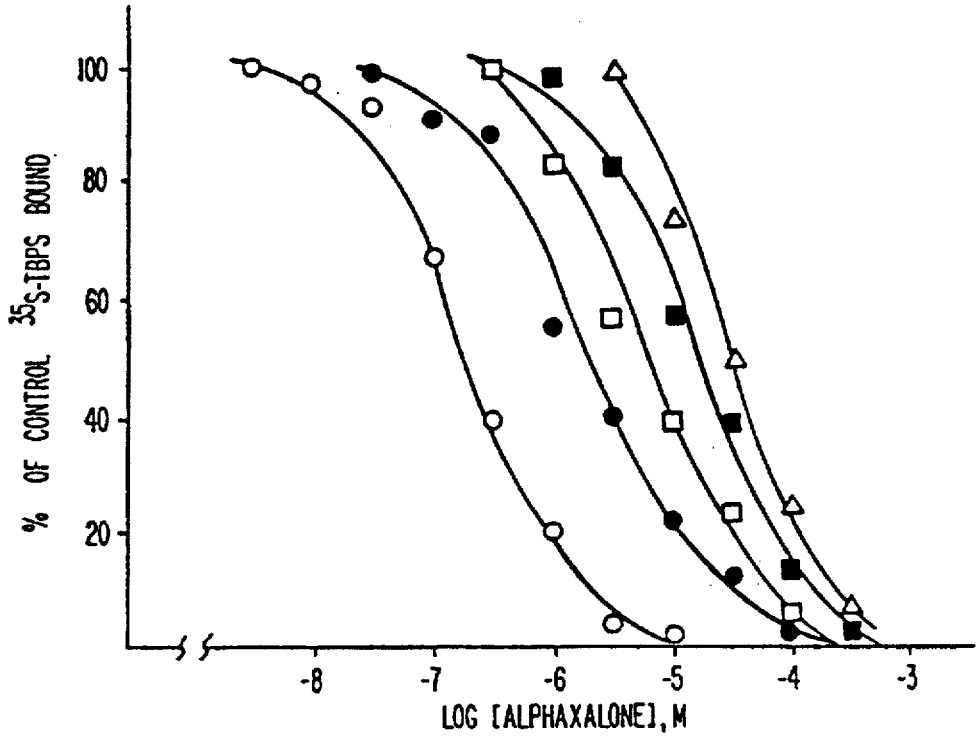
FIGS. 1A and 1B are plots of the binding percentage of [$^{35}$S] t-butylbicyclophosphorothionate vs. log concentration of alphaxalone and GABA.

The present invention is directed to a method, compositions, and compounds for modulating brain excitability. More particularly, the invention relates to the use of 3-hydroxylated-5-reduced steroid derivatives, acting at a newly identified site on the GBR complex, to modulate brain excitability in a manner that will alleviate stress, anxiety, and seizure activity. Compositions and compounds effective for such treatment are within the scope of the invention.

The compounds used in and forming part of the invention are modulators of the excitability of the central nervous system as mediated by their ability to regulate chloride ion channels associated with the GABA-benzodiazepine receptor complex. Applicants' experiments have established that the compounds used in and of the invention have anticonvulsant activity similar to the actions of known anxiolytic agents such as the benzodiazepines, but act at a distinct site on the GBR complex.

The relationship of endogenous metabolites of progesterone to processes associated with reproduction (estrus cycle and pregnancy) is well established (Marker, R. E., Kamm, O., and McGrew, R.V., "Isolation of epi-Pregnanol-3-one-20 from human pregnancy urine," J. Am. Chem. Soc. 59, 616–618, 1937). Prior to the present invention, however, it was not recognized how to treat disorders by modulating brain excitability. Therefore, this invention is directed to methods, compositions, and compounds to treat disorders by modulating brain excitability. Representative disorders treated in the present invention are epilepsy, anxiety, premenstrual syndrome (PMS), and post-natal depression (PND).

DETAILED DESCRIPTION OF THE INVENTION

The compounds of and used in the invention are various ester, oxime, and thiazolidine derivatives of 3-hydroxylated-5-reduced-pregnan-20-ones, 5-reduced-3,21-pregnanediol-20-ones, and 5-reduced-3,20-pregnandiols having a substituent in the 9-position, which derivatives are referred to as prodrugs by those skilled in the art of pharmaceutical preparations. The expression "prodrug" denotes a derivative of a known active drug whose derivative enhances the delivery characteristics and the therapeutic value of the drug and is transformed into the active drug by an enzymatic or chemical process; see Notari, R. E., "Theory and Practice of Prodrug Kinetics," Methods in Enzymology, 112:309–323 (1985) and Bodor, N., "Novel Approaches in Prodrug Design," Drugs of the Future, 6(3):165–182 (1981). It should be noted that some of the synthetic derivatives forming part of the present invention may not be true prodrugs because of their intrinsic activity.

Our studies (Gee, K. W., et al., "GABA-dependent modulation of the Cl ionophore by steroids in rat brain," European Journal of Pharmacology, 136:419–423, 1987) have demonstrated that the 3-hydroxylated-5-reduced steroids used in the invention are orders of magnitude more potent than others have reported (Majewska, M. D., et al., 1986, op. cit. and Harrison, N. L., et al., 1987, op. cit.) as modulators of the GBR complex. Our in vivo experimental data demonstrate that the high potency of these steroids allows them to be therapeutically useful in the modulation of brain excitability via the GBR complex. The most potent steroids useful in the present invention include major metabolites of progesterone. These steroids can be specifically used to modulate brain excitability in stress, anxiety, and seizure disorders. Furthermore, we have demonstrated that these steroids interact at a unique site on the GBR complex which is distinct from other known sites of interaction (i.e., barbiturate, benzodiazepine, and GABA) where therapeutically beneficial effects on stress, anxiety, sleep, and seizure disorders have been previously elicited (Gee, K. W. and Yamamura, H. I., "Benzodiazepines and Barbiturates: Drugs for the Treatment of Anxiety, Insomnia and Seizure Disorders," in Drugs in Central Nervous System Disorders, pages 123–147, D. C. Horwell, ed., 1985). The compounds of the present invention work in the same way.

The progesterone derivatives of this invention are those having the structural formula:

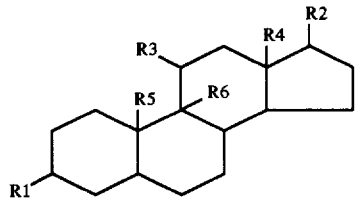

wherein R1 is:

(1) a pharmaceutically acceptable ester $$-Y-\overset{\overset{\displaystyle O}{\|}}{C}-R7,$$

wherein R7 is a $C_1$–$C_{20}$ straight chain, branched chain, or cyclic aliphatic radical, or aromatic radical, or heterocyclic radical, and Y is either a divalent oxygen or sulfur linkage. This ester is formed using reactions well known in the art between the hydroxyl group of the naturally occurring compounds discussed above with an organic acid, acid halide, acid anhydride, or ester, wherein the organic acids are for example: acetic, propionic, n and i-butyric, n and i and s and t-valeric, hexanoic, heptanoic, octanoic, nonanoic, decanoic, undecanoic, dodecanoic, cinnamic, benzylic, benzoic, maleic, fumaric, ascorbic, pamoic, succinic, bismethylenesalicylic, methanesulfonic, ethanedisulfonic, oxalic, tartaric, salicylic, citric, gluconic, aspartic, stearic, palmitic, itaconic, glycolic, p-aminobenzoic, glutamic, benzenesulfonic, cyclohexylsulfamic, and 1-methyl-1,4-dihydronicotinic; or (2) a pharmaceutically acceptable oxime =N-O-R8 radical wherein R8 is a $C_1$–$C_{20}$ straight chain, branched chain, or cyclic aliphatic radical, or aromatic radical, or heterocyclic radical, The radicals are identical to those given in the R7 definition. This oxime is formed by the reaction of a 3-oxo derivative of progesterone by methods well known to the art with an oxyamine; or (3) a pharmaceutically acceptable acyloxyalkyloxy

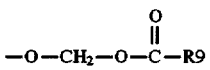

radical wherein R9 is a $C_1$–$C_{20}$ straight chain, branched chain, or cyclic aliphatic radical, or aromatic radical, or heterocyclic radical. The radicals are identical to those given in the R7 and R8 definitions. This acyloxyalkyloxy emobdiment is formed by the reaction of the 3-hydroxy group of the naturally-occurring compounds discussed above by methods well known to the art with an organic acyloxyalkyl halide (1–20 carbons) or aryloxyalkyl halide, and, in particular, acetyloxymethyl halide, diacetyloxymethyl halide, or [aminoacetyloxymethyl halide;]

*(4)hydroxyl;*

R2 is:

(1) OH or a pharmaceutically acceptable ester

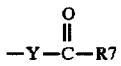

wherein R7 and Y are as defined previously or

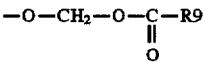

wherein R9 is as defined previously;

(2) a pharmaceutically acceptable

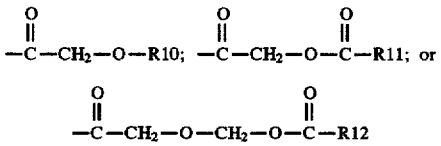

wherein R10, R11, and R12 individually are a $C_1$–$C_{20}$ straight chain, branched chain, or cyclic aliphatic radical, or aromatic radical, or heterocyclic radical, or an amide

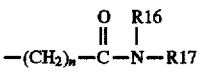

radical, wherein R16 and R17 are individually a $C_1$–$C_{20}$ straight chain, branched chain, or cyclic aliphatic radical or aromatic radical or heterocyclic radical and n=1–8. An example of a compound of the present invention wherein R11 is an amide is 5-alpha-pregnan-3-alpha-hydroxy-21-(N, N-diethylsuccinamate-20-one.

These compounds are formed by reacting the 21-hydroxy metabolite of progesterone in accordance with methods known in the art with an alkyl halide or organic acid, such as acetic, propionic, n and i-butyric, n and i and s and t-valeric, hexanoic, heptanoic, octanoic, nonanioc, decanoic, undecanoic, dodecanoic, cinnamic, benzylic, benzoic, maleic, fumaric, ascorbic, pamoic, succinic, bismethylenesalicylic, methanesulfonic, ethanedisulfonic, oxalic, tartaric, salicylic, citric, gluconic, aspartic, stearic, palmitic, itaconic, glycolic, p-aminobenzoic, glutamic, benzenesulfonic, cyclohexylsulfamic, and 1-methyl-1,4-dihydronicotinic;

(3) a pharmaceutically acceptable

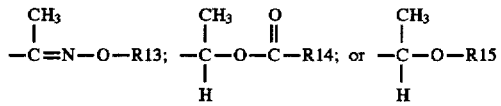

wherein R13, R14, and R15, individually are a $C_1$–$C_{20}$ straight chain, branched chain, or cyclic aliphatic radical, or aromatic radical, or heterocyclic radical. These compounds are prepared by reacting progesterone or the 20-hydroxy metabolite of progesterone with an alkyl halide or organic acid, such as acetic, propionic, n- and i-butyric, n- and i- and s- and t-valeric, hexanoic, heptanoic, octanoic, nonanoic, decanoic, undecanoic, dodecanoic, cinnamic, benzylic, benzoic, maleic, fumaric, ascorbic, pamoic, succinic, bismethylenesalicylic, methanesulfonic, ethanedisulfonic, oxalic, tartaric, salicylic, citric, gluconic, aspartic, stearic, palmitic, itaconic, glycolic, p-aminobenzoic, glutamic, benzenesulfonic, cyclohexylsulfamic, and 1-methyl-1,4-dihydronicotinic in accordance with known methods in the art;

(4) a pharmaceutically acceptable thiazolidine derivative of the 20-oxo position on progesterone having the formula:

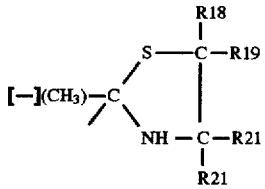

wherein R18 and R19 are individually a $C_1$–$C_{20}$ straight chain, branched chain, or cyclic aliphatic radical, or aromatic radical, or heterocyclic radical, and R20 and R21 are individually hydrogen or a $C_1$–$C_{20}$ straight chain, branched chain, or cyclic aliphatic radical, or aromatic radical, or heterocyclic radical, or

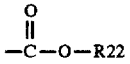

wherein R22 is H or a $C_1$–$C_{20}$ straight chain, branched chain, or cyclic aliphatic radical, or aromatic radical, or heterocyclic radical;

R3 is a hydroxy, keto, alkyloxy (1 to 18 carbons), aryloxy, or amino radical;

R4 is an alkyl (preferably 1 to 18 carbons), aryl, halo (such as fluoro, chloro, bromo, or iodo), or trifluroalkyl;

R5 is an alkyl (preferably 1 to 18 carbons), aryl, halo (such as fluoro, chloro, bromo, or iodo), or trifluoroalkyl and;

R6 is an alkyl (preferably 1 to 18 carbon atoms), aryl, halo (such as fluoro, chloro, bromo, or iodo), or trifluoroalkyl.

Representative alkyloxy groups for R3 include methoxy, ethoxy, propoxy, butoxy, octoxy, dodecoxy, and octadecoxy. Aryloxy groups useful as R3 moieties are phenoxy, tolyloxy, and the like.

Typical alkyl groups used a R4, R5, and R6 are methyl, ethyl, propyl, butyl, octyl, nonyl, dodecyl, t-butyl, and octadecyl. Representative aryl groups are phenyl, benzyl, tolyl, and naphthyl. Typical trifluoroalkyl groups include trifluoromethyl and trifluoroethyl.

Typical heterocyclic groups are 1-methyl-1,4-dihydronicotinic, [piperidinyl, pyridinyl, furanyl, thiophenyl] *piperidyl, pyridyl, furyl, thienyl*, and pyrazinyl.

The following examples are directed to the preparation of compounds forming part of and used in the present invention.

EXAMPLE 1

Preparation of 3α-hydroxy-5α-pregnan-20-one

The reaction was carried out under a dry N2 atmosphere. Potassium [trisamylborohydride] *trisiamylborohydride* solution (KS-[Selectide]*Selectride*) in THF (6 cc, 5.83 mmol) was introduced into a three neck round bottom flask and cooled to 0° C. 5α-Pregnan-3,20-dione (1.58 g, 5 mmol) dissolved in 10 reducing agent. The resulting mixture was stirred vigorously for 2 hours at 0° C. and then allowed to equilibrate to room temperature for 1 hour. The reaction was quenched with 3 ml of water and 7 ml of ethanol. The organoborane was oxidized with 5 ml of 6 M NaOH and 7 ml of 30% $H_2O_2$. The reaction mixture was saturated with anhydrous potassium carbonate, and the organic layer was separated. The aqueous phase was neutralized with 0.1 N HCl and extracted with 20 ml of chloroform twice. The combined organic layers were dried over anhydrous $MgSO_4$ and the solvent removed by rotary evaporation. Acetone was added to effect crystallization to produce a yield of 33%. The product has been identified by co-migration with authentic samples using silica based TLC and capillary GC. Melting point is 174°–175° C. Elemental analysis: Calc. C=79.19, H=10.76. Obs. C=78.86, H=10.70, NMR: 200 MHz ppm delta; 0.59 (s)(CH3), 0.77 (s)(CH3), 0.9–2.0 (m) (CH2), 2.1 (s)(CH3—C=O), 2.5 (t) (17-H), 4.02 (t) (3-H equatorial). The preparation method is a modification of the method shown in Gyermek et al., "Steroids CCCX. Structure-Activity Relationship of Some Steroidal Hypnotic Agents," J. Med. Chem., 11:117–125 (1968).

EXAMPLE 2

Preparation of 3-substituted esters

To a given amount of 3α-hydroxy-5α-pregnan-20-one dissolved in chloroform is added a two fold excess of the various acid chlorides (for example: acetyl, propionyl, or butyryl chloride). The reaction is refluxed for 10 to 15 minutes followed by neutralization with 1 N NaOH. Organic layers are washed with water, dried over $MgSO_4$, and reduced to dryness with rotary evaporation. The product is recrystallized from an acetone/hexane mixture.

EXAMPLE 3

Preparation of 20-spirothiazolidine derivatives

To a given amount of 3-substituted-5α-pregnan-20-one dissolved in 50 ml of pyridine is added a four fold excess of 1-cysteine or its methyl ester hydrochloride. After purging the system with nitrogen gas, the reaction mixture is stirred overnight at room temperature. The excess pyridine is evaporated and the residue dissolved in 150 ml of methylene chloride and washed with water twice. The organic layer is dried over $MgSO_4$. After removing the methylene chloride, the residue is boiled in methanol and filtered hot. The product is recrystallized from an acetone/hexane mixture. See U.S. Pat. No. 4,213,978.

EXAMPLE 4

Preparation of 3α-[(3-pyridiniumcarbonyl)oxy]-5α-pregnan-20-one.

Thionyl chloride (2 ml) is added to 0.7 g (5.7 mmol) of nicotinic acid and the mixture is refluxed for 3 hours. The excess thionyl chloride is removed under reduced pressure, and 10 ml of dry pyridine is then added to the cold residue followed by 1.44 g of 3α-hydroxy-5α-pregnan-20-one. The mixture is heated with continuous stirring at 100° C. for 4 hours. The pyridine is removed in vacuo, and 5 ml of methanol is added to the oily residue. The mixture is cooled, and the solid that crystallizes is filtered and recrystallized from methanol-acetone to give white crystals. See Bodor, "Improved Delivery Through Biological Membranes XIV: Brain-specific, Sustained Delivery of Testosterone Using a Redox Chemical Delivery System," J. Pharmaceutical Sciences, 73(3): 385–389 (1984).

EXAMPLE 5

Preparation of 3α-[(1-methyl-3-pyridiniumcarbonyl) oxy]-5α-pregnan-20-one

To a solution of 1.0 g of 3α-(3-pyridiniumcarbonyl)oxy] -5α-pregnan-20-one in 15 ml of acetone is added 1 ml of methyl iodide, and the mixture is heated at reflux overnight. The yellow material that separates is removed by filtration, washed with acetone and crystallized from methanol-ether to yield yellow crystals. See the Bodor article referred to in Example 4.

It will be obvious to one skilled in the art that the above described compounds may be present as [diastereo isomers] *diastereoisomers* which may be resolved into d or 1 optical isomers. Resolution of the optical isomers may be conveniently accomplished by gas or liquid chromatography or isolation from natural sources. Unless otherwise specified herein, including the claims, reference to the compounds of the invention, as discussed above, is intended to include all isomers, whether separated or mixtures thereof.

Where isomers are separated, the desired pharmacological activity will often predominate in one of the isomers. As disclosed herein, these compounds display a high degree of stereospecificity. In particular, those compounds having the greatest affinity for the GABA-benzodiazepine receptor complex are those with 3-alpha-substituted-5-alpha-pregnane steroid skeletons. In addition, 3-alpha-substituted-5-beta-pregnane skeletons have been demonstrated to be active. The preferred prodrugs include 3α-hydroxy-5α-pregnan-20-spirothiazolidine and N-methyl-nicotinyl esters of 3α-hydroxy-5α-pregnan-20-one.

The compounds of and used in the invention, that being the nontoxic pharmaceutically acceptable synthetic "prodrug" forms of progesterone have hitherto unknown activity in the brain at the GABA-benzodiazepine receptor complex. The present invention takes advantage of the understanding of this previously unknown activity.

The compounds of the invention may be prepared by any known technique. For example, the naturally occurring metabolites of progesterone may be extracted from various animal excretion sources, e.g., urine. Such extractions are conducted using the following steps: (i) hydrolysis of the urine with HCl; (ii) extraction with toluene; (iii) removal of acidic material from the toluene extract; (iv) elimination of substances other than pregnanediol from the neutral toluene-soluble fraction by precipitations from ethanolic solution with dilute NaOH and with water; and (v) weighing of the purified pregnanediol obtained. See Marrian et al., "The Isolation of Pregnane-3α-ol-20-one," Biochem., 40:376–380 (1947). These extracted compounds may then be chemically altered to form the desired synthetic derivative, or used directly.

The pharmaceutical compositions of this invention are prepared in conventional dosage unit forms by incorporating an active compound of the invention or a mixture of such compounds, with a nontoxic pharmaceutical carrier according to accepted procedures in a nontoxic amount sufficient to produce the desired pharmacodynamic activity in a subject, animal or human. Preferably, the composition contains the active ingredient in an active, but nontoxic amount, selected from about 50 mg to about 500 mg of active ingredient per dosage unit. This quantity depends on the specific biological activity desired and the condition of the patient. The most desirable object of the composition and methods is in the treatment of PMS, catamenial epilepsy, and PND to ameliorate or prevent the attacks of anxiety, muscle tension, and depression common with patients suffering from these central nervous system abnormalities.

The pharmaceutical carrier employed may be, for example, either a solid, liquid, or time release (see e.g. Remington's Pharmaceutical Sciences, 14th Edition, 1970). Representative solid carriers are lactose, terra alba, sucrose, talc, gelatin, agar, pectin, acacia, magnesium stearate, stearic acid, microcrystalline cellulose, polymer hydrogels and the like. Typical liquid carriers are syrup, peanut oil, and olive oil and the like emulsions. Similarly, the carrier or diluent may include any time-delay material well known to the art, such as glyceryl monostearate or glyceryl distearate alone or with a wax, microcapsules, microspheres, liposomes, and hydrogels.

A wide variety of pharmaceutical forms can be employed. Thus, when using a solid carrier, the preparation can be tableted, placed in a hard gelatin capsule in powder or pellet form, or in the form of a troche, lozenge, or suppository. When using a liquid carrier, the preparation can be in the form of a liquid, such as an ampule, or as an aqueous or nonaqueous liquid suspension. Liquid dosage forms also need pharmaceutically acceptable preservatives and the like. In addition, because of the low doses that will be required as based on the in vitro data disclosed herein, timed release skin patches are also a suitable pharmaceutical form for topical administration.

The method of producing anxiolytic, or anticonvulsant activity, in accordance with this invention, comprises administering to a subject in need of such activity a compound of the invention, usually prepared in a composition as described above with a pharmaceutical carrier, in a nontoxic amount sufficient to produce said activity.

During menses, the levels of excreted metabolites varies approximately fourfold (Rosciszewska, et al., op. cit.). Therefore, therapy for controlling symptoms involves maintaining the patient at a more uniform level of progesterone metabolite. Plasma levels of active and major metabolites are monitored during pre-menses and post-menses of the patient. The amount of the compounds, either singly or mixtures thereof, of the invention administered reflects the physiological concentrations which naturally occur post-menses. The route of administration may be any route that effectively transports the active compound to the GABA-benzodiazepine receptors that are to be stimulated. Administration may be carried out parenterally, rectally, intravaginally, intradermally, [subliqually] *sublingually*, or nasally; the dermal route is preferred. For example, one dose in a skin patch may supply the active ingredient to the patient for a period of up to one week.

The in vitro and in vivo experimental data show that the naturally-occurring metabolites of progesterone and their derivatives interact with high affinity at a novel and specific recognition site on the GBR complex to facilitate the conductance of chloride ions across neuronal membranes sensitive to GABA (Gee et al, 1987).

To those skilled in the art, it is known that the modulation of [$^{35}$S] t-butylbicyclophosphorothionate ([$^{35}$S] TBPS) binding is a measure of the potency and efficacy of drugs acting at the GBR complex, which drugs may be of potential therapeutic value in the treatment of stress, anxiety, and seizure disorders (Squires, R. F., et al., "[]][$^{35}$S]t-Butylbicyclophophorothionate binds with high affinity to brain-specific sites coupled to a gamma aminobutyric acid-A and ion recognition site," Mol. Pharmacol., 23:326, 1983; Lawrence, L. J., et al., "Benzodiazepine anticonvulsant action: gamma-aminobutyric acid-dependent modulation of the chloride ionophore," Biochem. Biophys. Res. Commun., 123:1130–1137, 1984; Wood, et al., "In vitro characterization of benzodiazepine receptor agonists, antagonists, inverse agonists and agonist/antagonists," J. Pharmacol. Exp. Ther., 231:572–576, 1984). We performed an assay to determine the modulation of [$^{35}$S] TBPS as effected by the compounds of the invention and found that these compounds have high potency and efficacy at the GBR complex, with stringent structural requirements for such activity.

The procedures for performing this assay are fully discussed in: (1) Gee, et al., 1987 op. cit.; and (2) Gee, K. W., L. J. Lawrence, and H. I. Yamamura, "Modulation of the chloride ionopore by benzodiazepine receptor ligands influence of gamma-aminobutyric acid and ligand efficacy," Molecular Pharmacology, 30, 218, 1986. These procedures were performed as follows:

Brains from male Sprague-Dawley rats were removed immediately following killing and the cerebral cortices dissected over ice. A $P_2$ homogenate was prepared as previously described (Gee, et al., 1986, op. cit.). Briefly, the cortices were gently homogenized in 0.32M sucrose followed by centrifugation at 1000× g for 10 minutes. The supernatant was collected and centrifuged at 9000×g for 20 minutes. The resultant $P_2$ pellet was suspended as a 10% (original wet weight/volume) suspension in 50 mM Na/K phosphate buffer (pH 7.4)+200 mM NaCl to form the homogenate.

One hundred microliter aliquots of the $P_2$ homogenate (0.5 milligrams (mg) protein) were incubated with 2 nanomolar (nM) TBPS [$^{35}$S]TBPS (70–110 curies/millimole;, New England Nuclear, Boston, Mass.) in the presence or absence of the naturally occurring steroids and their synthetic derivative prodrugs to be tested. The tested compounds were dissolved in dimethylsulfoxide (Baker Chem. Co., Phillipsbury, N.J.) and added to the incubation mixture in 5 microliter aliquots. The incubation mixture was brought to a final volume of 1 milliliter (ml) was buffer. Non-specific binding was defined as binding in the presence of 2 micromolar TBPS. The effect and specificity of GABA (Sigma Chem. Co., St. Louis, Mo.) was evaluated by performing all assays in the presence of 5 micromolar GABA±(+)-bicuculline (Sigma Chem. Co.). Incubations maintained at 25° C. for 90 minutes (steady state conditions) were terminated by rapid filtration through glass fiber filters (No. 32, Schleicher and Schuell, Keene, N.H.). Filter bound radioactivity was quantitated by liquid scintillation spectrophotometry. Kinetic data and compound/[$^{35}$S]TBPS dose-response curves were analyzed by non-linear regression using a computerized iterative procedure to obtain rate constants and $IC_{50}$ (concentration of compound at which half-maximal inhibition of basal [$^{35}$S]TBPS binding occurs) values.

Figure 1B:
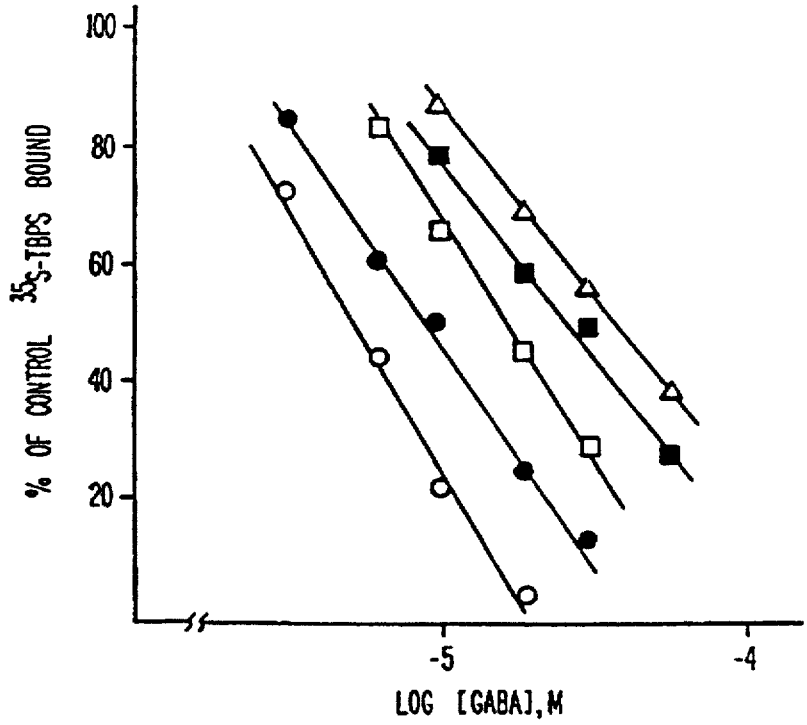

The experimental data obtained for this assay are also published in Gee, et al., 1987. The data discussed in this reference are shown as plots in FIGS. 1A and 1B. These plots show the effect of (+)-bicuculline on alphaxalone (1A) and GABA (1B) modulation of 2 nanomolar [$^{35}$S]TBPS binding to rat cerebral cortex. In these FIGS, (○) represents control without bicuculline: (●) represents 0.5 micromolar bicuculline; (□) represents 1.0 micromolar bicuculline; (■) represents 2.0 micromolar bicuculline; and (Δ) represents 3.0 micromolar bicuculline. In this experiment, the effect of (+)-bicuculline on the ability of alphaxalone or GABA to inhibit the binding of [$^{35}$S]TBPS was determined. Bicuculline is known to be directly competitive with GABA and a classical parallel shift in the dose-response curves is observed in FIG. 1B. In contrast, the steroid binding site is distinct from the GABA/bicuculline site in FIG. 1A. The shift in dose-response curves induced by (+)-bicuculline when the inhibition of [$^{35}$S]-TBPS binding is caused by alphaxalone is not linear. This indicates that the GABA and steroid sites do not overlap.

An assay was performed to determine the effect of pentobarbital on the dissociation kinetics of [$^{35}$S]TBPS in rat cerebral cortical membranes. This assay was performed in accordance with the procedures outlined above. These data indicate that the site of action of the compounds of the invention is unique and distinct from the previously known sites of action for the barbiturates and the BZs. The results of the in vitro assay are shown in FIGS. 2A and 2B. The plots in FIGS. 2A and 2B show the effect of pentobarbital, alphaxalone, or 5-alpha-pregnan-3-alpha-hydroxy-20-one on the dissociation kinetics for 2 nanomolar [$^{35}$S]-TBPS in cortical P2 homogenates. Dissociation of bound [$^{35}$]TBPS was initiated by 2 micromolar TBPS in all cases. Pentobarbital (FIG. 2A) at 30 micromolar induces a biphasic dissociation mechanism which is absent for alphaxalone (300 nanomolar) and 5-alpha-pregnan-3-alpha-hydroxy-20-one (20 nanomolar) (FIG. 2B).

The kinetic rate constants and half lives obtained by this assay are set forth in Table 1. The information presented in Table 1 shows that the barbiturate induces a shift in [teh] *the* half life of dissociation and the proportion of slow and rapidly dissociating components—hallmark effects of therapeutically useful GABA agonists, barbiturates, and BZs on [$^{35}$S]TBPS binding (Gee, et al., 1986; Maksay, G. & Ticku, M., "Dissociation of [$^{35}$S]t-butylbicyclophoporothionate binding differentiates convulsant and depressant drugs that [odulate] *modulate* GABAergic transmission," J. [Neruochem] *Neurochem*, 44:480–486, 1985). In contrast, the progesterone metabolite 5-alpha-pregnan-3-alpha-ol-20-one and the progestin alphaxalone do not influence the dissociation kinetics of [$^{35}$S]TBPS binding. The steroid and barbiturate sites are, therefore, distinct.

TABLE 1

| | $t_{1/2}$ (min) | | $k_{-1}$ ($min^{-1}$) | | Total percentage of specific sites | |
|---|---|---|---|---|---|---|
| Conditions | S | R | S | R | S | R |
| Control | 50 ± 4 | 6 ± 1 | 0.0145 ± 0.0008 | 0.131 ± 0.016 | 73 ± 2 | 30 ± 2 |
| 30 nM Na pentobarbital | 38 ± 3 | 4.4 ± 0.3 | 0.0186 ± 0.0015 | 0.158 ± 0.013 | 61 ± 6* | 48 ± 6** |
| 300 nM Alphaxalone | 67 ± 12 | 4.9 ± 1 | 0.0120 ± 0.003 | 0.180 ± 0.040 | 73 ± 4 | 34 ± 5 |
| 20 nM a-OH—DHP | 76 ± 11 | 6.4 ± 1 | 0.011 ± 0.002 | 0.122 ± 0.030 | 68 ± 3 | 35 ± 3 |

Significantly different from control @ *P < 0.05 and **P < 0.01 by Student's [t-gest]*t-test*. S and R represent slowly and rapidly dissociating components respectively.

Figure 3:
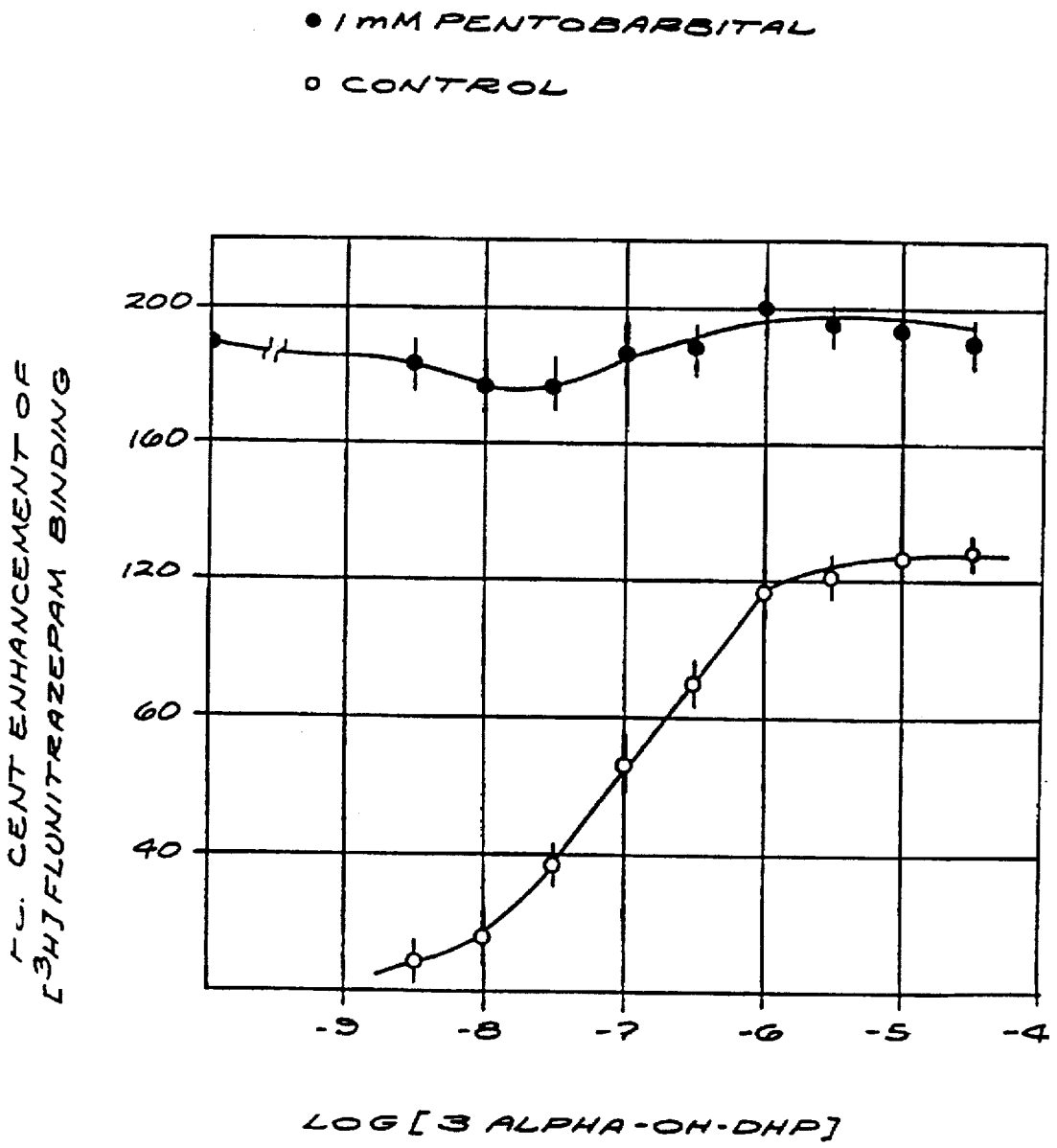
FIG. 3 is a plot showing the effect of a single dosage of pentobarbital on 5-alpha-pregnan-3-alpha-ol-20-one modulation of [$^{3}$H] flunitrazepam binding in rat hippocampal homogenates.

Furthermore, 5-alpha-pregnan-3-alpha-ol-20-one does not interact with pentobarbital in the enhancement of the binding of [$^{3}$H] flunitrazepam to the BZ receptor in the cortical brain homogenates (FIG. 3) indicating that steroids and barbiturates do not share a common site of action. The data of FIG. 3 were obtained by performing an assay to determine the effect of a single concentration of pentobarbital (1.0 millimolar) on 5-alpha-pregnan-3-alpha-ol-20-one modulation of 0.25 nM [$^{3}$H] flunitrazepam ([$^{3}$H]FLU) binding to the BZ receptor in rat hippocampal homogenates. This assay was performed in accordance with the procedures outlined above. Each point on the plot of FIG. 3 represents the mean +SEM of 4–6 independent determinations. The data points in both curves are expressed as percent enhancements of [$^{3}$H]FLU binding, which is defined as the percentage of [$^{3}$H]FLU bound in the absence of 5-alpha-pregnan-3-alpha-ol-20-one under the control conditions minus 100%. All assays were performed in the absence of GABA.

The above data demonstrate that the compounds of and used in the invention interact with a novel site distinct from previously defined regulatory sites on the GBR complex.

Various compounds were screened to determine their potential as modulators of [$^{35}$S]TBPS binding in vitro. These assays were performed in accordance with the above discussed procedures. Based on these assays, we have established the structure-activity requirements for their specific interaction at the GBR complex and their rank order potency and efficacy (Table 2 below).

TABLE 2

| COMPOUND | | CONTROL $IC_{50}$ (nM) | +5 μM GABA $IC_{50}$ (nM) | MAXIMAL INHIBITION |
|---|---|---|---|---|
| 5α-PREGNAN-3α-[DL]*OL*-20-ONE (EPIALLOPREGNANOLONE) | | 230 | 17 | 100 |
| 5α-PREGNAN-3α,20-DIOL (PREGNANDIOL) | | 359 | 82 | 52 |
| 5α-PREGNAN-3α-[DL]*OL*-11.20-DIONE (ALPHAXALONE) | | 11000 | 264 | 100 |
| 5α-ANDROSTAN-3α, 17β-DIOL | | 15000 | 1000 | 100 |
| PROGESTERONE | | $>10^5$ | 5200 | 100 |
| 5α-PREGNAN-3α,21-DIOL-11,20-DIONE | | $>10^5$ | 5500 | 100 |
| 5α-ANDROSTAN-17β-[DL]*OL*-3-ONE | | $>10^5$ | 18000 | 52 |
| 5α-PREGNAN-3β-[DL]*OL*-20-ONE (ALLOPREGNANOLONE) | | INACTIVE | $>10^5$ | 33 |
| 5α-PREGNEN-3β-[DL]*OL*-20-ONE (PREGNENOLONE) | | INACTIVE | $>10^5$ | 30 |

TABLE 2-continued

| COMPOUND | | CONTROL $IC_{50}$ (nM) | +5 μM GABA $IC_{50}$ (nM) | MAXIMAL INHIBITION |
|---|---|---|---|---|
| 4-PREGNEN-11β,21-DIOL-3,20-DIONE (CORTI-COSTERONE) | 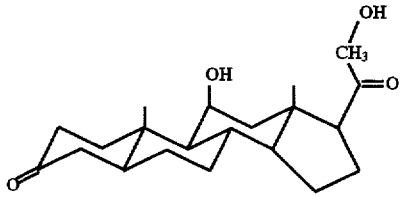 | INACTIVE | $>10^5$ | 21 |
| 17β-ESTRADIOL | 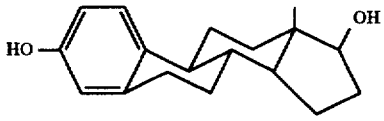 | INACTIVE | INACTIVE | 0 |
| CHOLESTEROL | 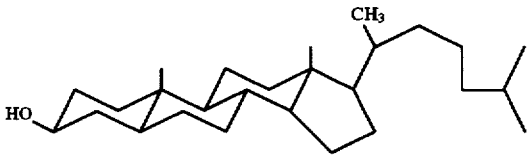 | INACTIVE | INACTIVE | 0 |

Figure 4:
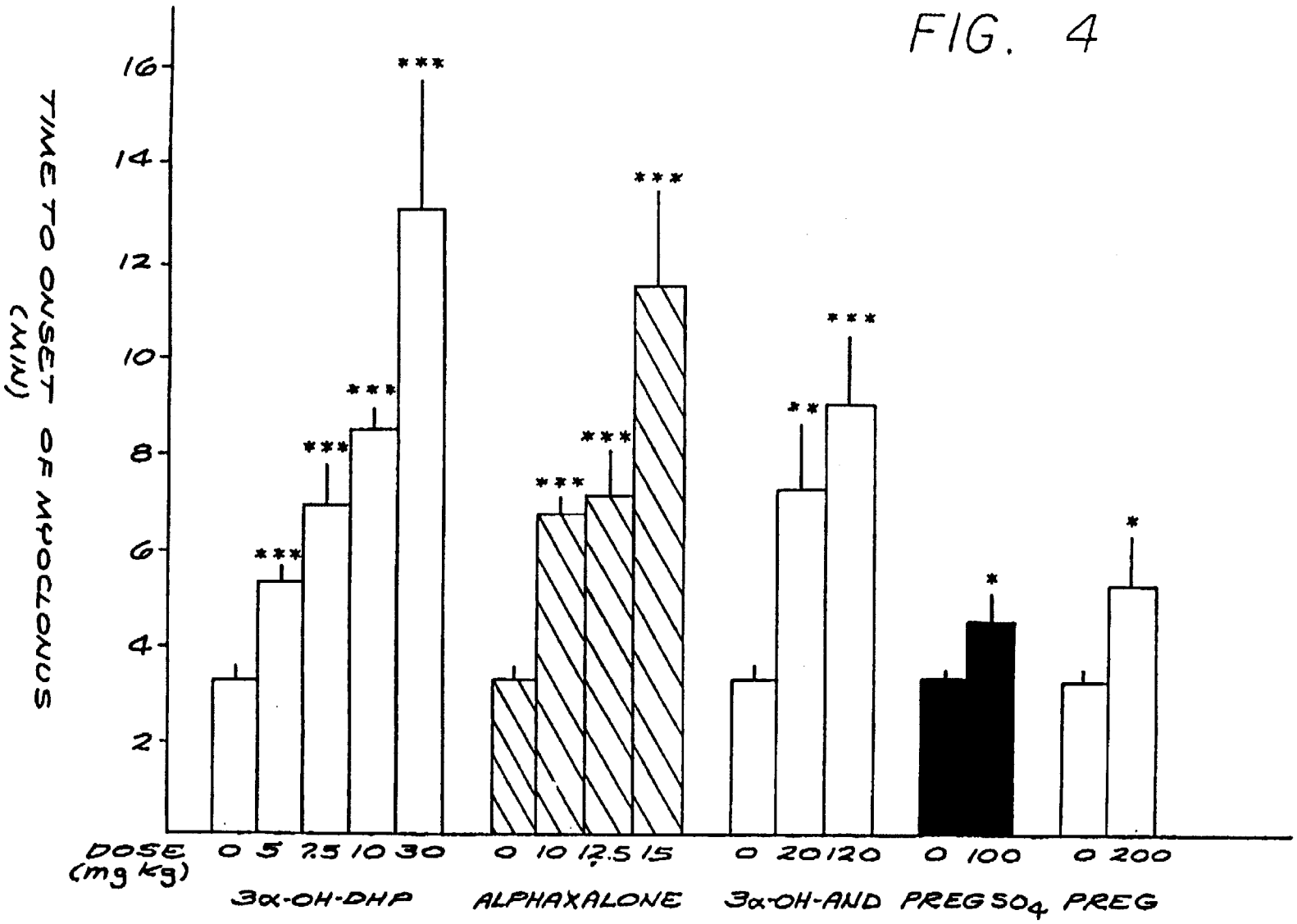
FIG. 4 is a bar graph of the time to onset of myoclonus vs. different concentrations of steroid compounds useful in the present invention.

Experiments were also performed to determine the physiological relevance of these interactions by measuring the ability of the compounds of and used in the invention to modulate TBPS-induced convulsions in Swiss-Webster mice. Mice were injected with various doses of the test compounds of the invention, as indicated in FIG. 4, 10 minutes prior to the injection of TBPS. The time to onset of myoclonus (presence of forelimb clonic activity) induced by TBPS was determined by observing each mouse of a period of 45 minutes. Significant differences between the time to onset in control mice vs. steroid-treated mice were determined by Student's t-test. The relative tank order potency and efficacy of these steroids in vivo were well correlated with those values determined in vitro. The anticonvulssant and toxicological profiles of [5α-pregnan-3α-5 ol-20-one] *5α-pregnan-3α-ol-20-one* (3α-OH-DHP) were determined. In the anticonvulsant screen, mice were injected with various doses of 3α-OH-DHP or vehicle (dimethylsulfoxide) 10 minutes prior to the administration of the following chemical convulsants: metrazol (85 mg/kg); (+)bicuculline (2.7 mg/kg); picrotoxin (3.15 mg/kg); strychnine (1.25 mg/kg); or vehicle (0.9% saline). Immediately after the injection of convulsant or vehicle, the mice were observed for a period of 30 to 45 minutes. The number of animals with tonic and/or clonic convulsions was recorded. In the maximal electroshock test, 50 mA of current at 60 Hz was delivered through corneal electrodes for 200 msec. The ability of 3α-OH-DHP to abolish the tonic component was defined as the endpoint. Sedative potential was determined by a rotorod test 10 minutes after the injection of 3α-OH-DHP where the number of mice staying on a rotating (6 rpm) rod for ≧1 minute in each of 3 trials was determined. The $ED_{50}$ (the dose at which the half-maximal effect occurs) dose was determined for each screen. The acute $LD_{50}$ (the dose that is lethal to one half of the animals tested) was determined by counting survivors 48 hours after the administration of 3α-OH-DHP. The results are presented in Table 3, infra, and demonstrate that 3α-OH-DHP, in comparison to other clinically useful anticonvulsants, is highly effective with a profile similar to that of the benzodiazepine clonazepam. The sedative liability at anticonvulsant doses is low as shown by comparing the $ED_{50}$ values for the rotored test and (+)bicuculline-induced seizures. The therapeutic index (ratio of $LD_{50}$ to $ED_{50}$) for 3α-OH-DHP is >122 when based on the $ED_{50}$ against (+)bicuculline-induced seizures, thus indicating very low toxicity. These observations demonstrate the therapeutic utility of these compounds as modulators of brain excitability, which is in correspondence with their high affinity [interactio] *interaction* with the GBR complex in vitro.

TABLE 3

Anticonvulsant and acute toxicological profile of 3α-OH—DHP and those of selected clinically useful anticonvulsants in mice.

| Compound | RR | $ED_{50}$* MES | MTZ | BIC | PICRO | STR | $LD_{50}$ |
|---|---|---|---|---|---|---|---|
| 3α-OH—DHP | 40–100 | >300 | 18.8 ± 1.1 | 4.1 ± 1.7 | 31.7 ± 1.1 | >300 | >500 |
| Clonazepam | 0.184 | 93 | 0.009 | 0.0086 | 0.043 | NP | >6000 |
| Phenobarbital | 69 | 22 | 13 | 38 | 28 | 95 | 265 |
| Phenytoin | 65 | 10 | NP | NP | NP | ** | 230 |
| Progabide*** | — | 75 | 30 | 30 | 105 | 75 | 3000 |
| Valproate | 426 | 272 | 149 | 360 | 387 | 293 | 1105 |

*All $ED_{50}$ values for 3α-OH—DHP include the 95% confidence limits. The abbreviations are RR (Rotorod); MES (maximal electroshock); MTZ (metrazol); BIC (bicuculline); PICRO (picrotoxin); STR (strychnine); NP (no protection).

TABLE 3-continued

Anticonvulsant and acute toxicological profile of 3α-OH—DHP and those of selected clinically useful anticonvulsants in mice.

| Compound | RR | $ED_{50}$* MES | MTZ | BIC | PICRO | STR | $LD_{50}$ |
|---|---|---|---|---|---|---|---|

**Maximum protection of 50% at 55–100 mg/kg.

***The chemical convulsants in the progabide studies were administered i.v., all data from Worms et al., Gammaaminobutyric acid (GABA) receptor stimulation. I. Neuropharacolocigical profiles of progabide (SL 76002) and SL 75102, with emphasis on their anticonvulsant spectra. Journal of Pharmacology and Experimental Therapeutics 220: 660–671, 1982. All remaining anticonvulsant data are from Swinyard & Woodhead. General principles; experimental detection, quantification and evaluation of anticonvulsants, in: Antiepileptic Drugs. D. M. Woodbury, J. K. Penry. and C. E. Pippenger, eds., p. 111. (Raven Press, New York). 1982.

The correlations between reduced levels of progesterone and the symptoms associated with PMS, PND, and catamenial epilepsy (Backstrom, et al., 1983, op. cit.; Dalton, K., 1984, op. cit.) led to the use of progesterone in their treatment (Mattson, et al., 1984; and Dalton, 1984). However, progesterone is not consistently effective in the treatment of the aforementioned syndromes. For example, no dose-response relationship exists for progesterone in the treatment of PMS (Maddocks, et al, 1987, op. cit.). These results are predictable when considered in light of the results of our in vitro studies which demonstrate that progesterone has very low potency at the GBR complex, as seen in Table 2, compared to certain metabolites of progesterone.

The beneficial effect of progesterone is probably related to the variable conversion of progesterone to the active progesterone metabolites. The use of specific progesterone metabolites in the treatment of the aforementioned syndromes is clearly superior to the use of progesterone based upon the high potency and efficacy of the metabolites and their derivatives (See Gee, et al., 1987, and Table 2 above).

Figure 5:
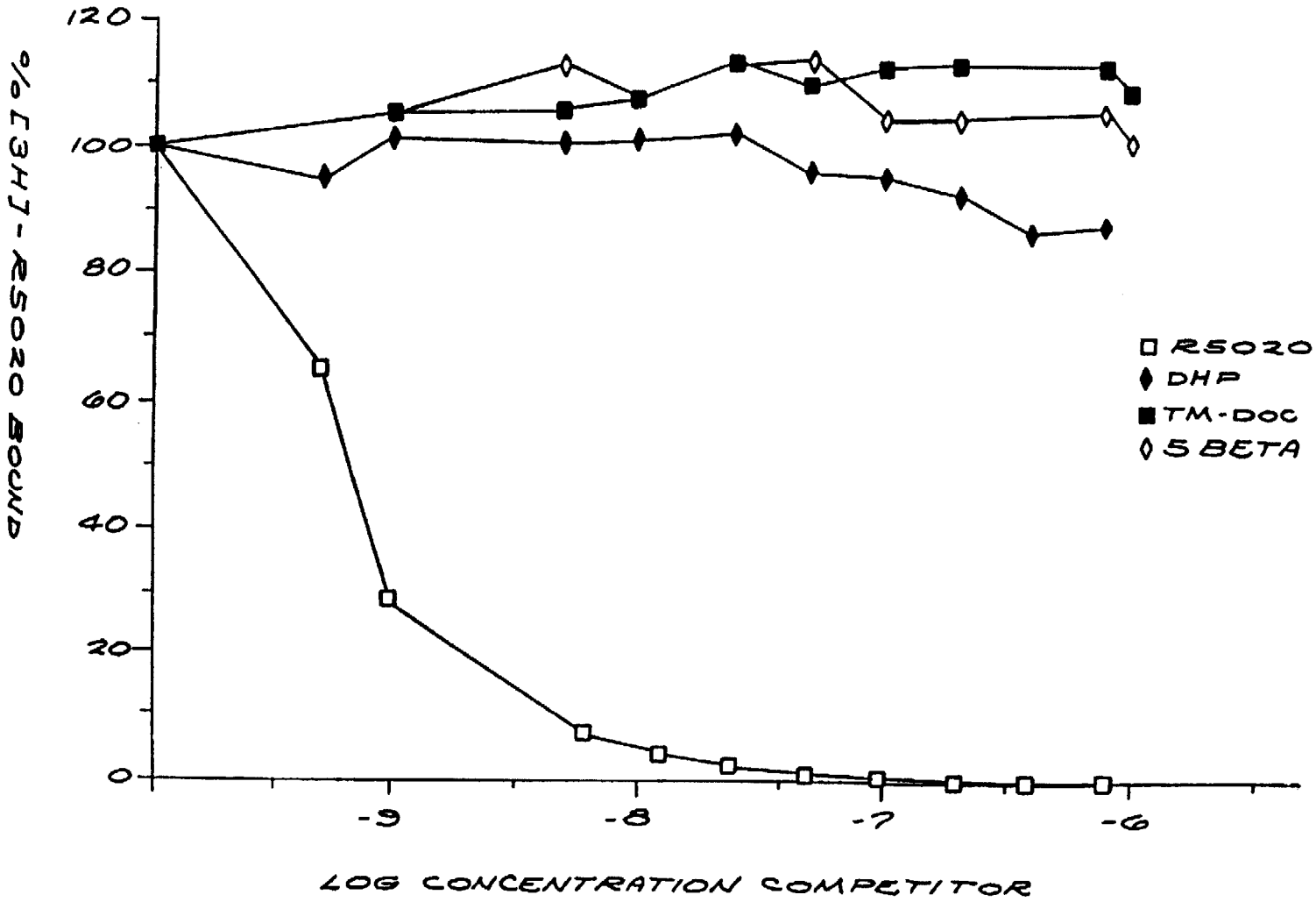
FIG. 5 is a plot showing the effect of progesterone metabolites and promogesterone (progestin R5020) on [$^{3}$H] R5020 binding to the progesterone receptor in rat uterus.

It has also demonstrated that the compounds of and used in the invention lack hormonal side effects by the lack of affinity of these compounds of the invention for the progesterone receptor (FIG. 5). The data plotted in FIG. 5 were obtained by performing assays in accordance with the procedures outlined above to determine the effect of progesterone metabolites and the progestin R5020 on the binding of [$^3$H]R5020 to the progesterone receptor in rat uterus. All points on the plot of FIG. 5 represent the mean of triplicate determinations. The following compounds are those listed in FIG. 5: 5-alpha-pregnan-3-alpha-ol-20-one (DHP), 5-alpha-pregnan-3-alpha,21-diol-20-one (Th-DOC), and 5-beta-pregnane-3-alpha,20 diol (5 BETA).

While the preferred embodiments have been described and illustrated, various substitutions and modifications may be made thereto without departing from the scope of the invention. Accordingly, it is to be understood that the present invention has been described by way of illustration and not limitation.

We claim:

1. A method for modulating excitability of the central nervous system as mediated by the ability to regulate chloride ion channels associated with the GABA-benzodiazepine receptor complex comprising administering to a patient in need of such treatment a central nervous system [excitabiilty] *excitability* modulating pharmaceutically effective amount of a [3-hydroxylated-5-reduced] neuroactive steroid compound that activates the GABA-benzodiazepine receptor-chloride ionophore complex by attaching to a brain receptor site other than any previously known recognition site of said complex, but associated with and still activating said complex, of the formula

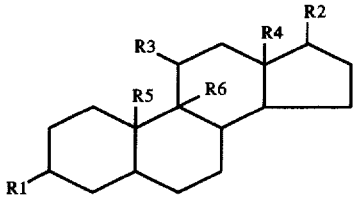

wherein R1 is selected from the group consisting of hydroxyl,

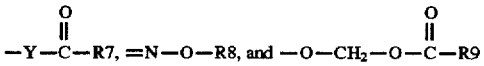

wherein R7, R8, and R9 are individually a $C_1$–$C_{20}$ straight chain aliphatic radical, [$C_1$] *a* $C_3$–$C_{20}$ branched chain aliphatic radical, [or] *a* $C_3$–$C_{10}$ cyclic aliphatic radical, [or $C_3$] *a* $C_6$–$C_{10}$ aromatic radical, or a heterocyclic radical selected from the group consisting of 1-methyl-1,4-dihydronicotinoyl, [piperidinyl, pyridinyl, furanyl, thiphenyl] *piperidyl, pyridyl, furyl, thienyl*, and [pyrzinyl] *pyrazinyl*, and Y is —O— or —S—;

R2 is selected from the group consisting of OH, acetyl, [2-hydroxyethanonyl] *2-hydroxyethanoyl*, 1-hydroxyethyl,

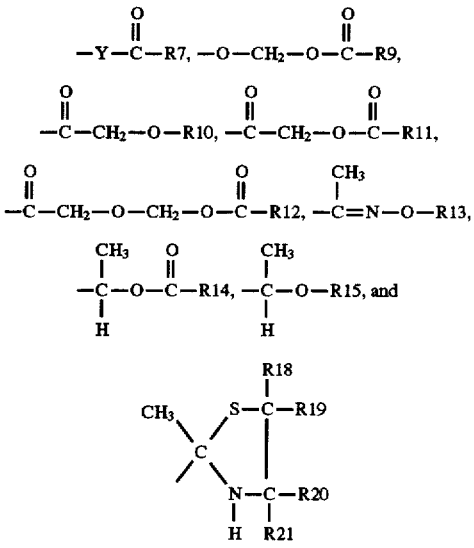

wherein Y, R7, and R9 are as defined previously and R10, R11,R12, R13, R14, R15, R18, R19, R20, and R21 are individually a $C_1$–$C_{20}$ straight chain aliphatic radical, [$C_1$] *a* $C_3$–$C_{20}$ branched chain [alipahtic] *aliphatic* radical, [or] *a* $C_3$–$C_{10}$ cyclic aliphatic radical [or $C_3$] *a* $C_6$–$C_{10}$ aromatic radical, or a heterocyclic radical selected from the group consisting of 1-methyl-1,4-dihydronicotinoyl, [piperidinyl, pyridinyl, furanyl, thiophenyl] *piperidyl, pyridyl, furyl, thienyl*, and pyrazinyl with the provisos that (1) R10, R11, and R12 may also individually be an amide

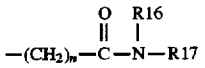

radical wherein R16 and R17 individually are a $C_1$–$C_{20}$ straight chain aliphatic radical, [$C_1$] *a* $C_3$–$C_{20}$ branched cain aliphatic radical, [or] *a* $C_3$–$C_{10}$ cyclic aliphatic radical, [or $C_3$] *a* $C_6$–$C_{10}$ aromatic radical, or a heterocyclic radical selected from the group consisting of 1-methyl-1,4-dihydronicotinoyl, [piperidinyl, pyridinyl, furanyl, thienyl] *piperidyl, pyridyl, furyl, thienyl*, and pyrazinyl, and n=1 to 8 and (2) R20 and R21 may also individually by [H] *hydrogen*, or

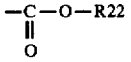

wherein R22 is [H or] *hydrogen*, a $C_1$–$C_{20}$ straight chain aliphatic radical, [$C_1$] *a* $C_3$–$C_{20}$ branched chain aliphatic radical, [or] *a* $C_3$–$C_{10}$ cyclic aliphatic radical, [or $C_3$] *a* $C_6$–$C_{10}$ aromatic radical, or a heterocyclic radical selected from the group consisting of 1-methyl-1,4-dihydronicotinoyl, [piperidinyl, pyridinyl, furanyl, thiophenyl] *piperidyl, pyridyl, furyl, thienyl*, and pyrazinyl[, and n is an integer of 1 to 8];

R3 is selected from the group consisting of hydrogen, hydroxy, keto, [$C_1$–$C_{18}$ alkyloxy,] aryloxy, [and] amino, *and* $C_1$–$C_{18}$ *alkyloxy*; and R4, R5, and R6 individually are selected from the group consisting of [$C_1$–$C_{18}$ alkyl,] aryl, halo, [and] trifluoroalkyl, *and* $C_1$–$C_{18}$ *alkyl*.

2. The method of claim 1 wherein said pharmaceutically effective amount is sufficient to alleviate stress in said patient.

3. The method of claim 1 wherein said pharmaceutically effective amount is sufficient to alleviate anxiety in said patient.

4. The method of claim 1 wherein said pharmaceutically effective amount is sufficient to alleviate seizure activity in said patient.

5. The method of claim 1 wherein said pharmaceutically effective amount is from about 50 mg to about 500 mg per dosage unit.

6. A compound of the formula:

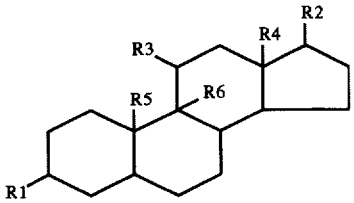

wherein R1 is selected from the group consisting of hydroxyl,

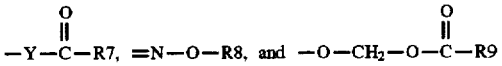

wherein R7, R8, and R9 are individually a $C_1$–$C_{20}$ straight chain aliphatic radical, [$C_1$] *a* $C_3$–$C_{20}$ branched chain aliphatic radical, [or] *a* $C_3$–$C_{10}$ cyclic aliphatic radical, [or $C_3$] *a* $C_6$–$C_{10}$ aromatic radical, or a heterocyclic radical selected from the group consisting of 1-methyl-1,4-dihydronicotinoyl, [piperdinyl, pyridinyl, furanyl, thiphenyl] *piperidyl, pyridyl, furyl, thienyl*, and [pyrzinyl] *pyrazinyl*, and Y is —O— or —S—;

R2 is selected from the group consisting of OH, acetyl [2-hydroxyethanonyl] *2-hydroxyethanoyl*, 1-hydroxyethyl,

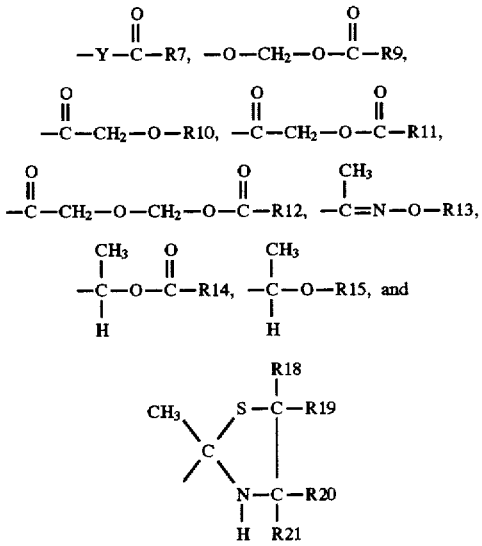

wherein Y, R7, and R9 are as defined previously and R10, R11, R12, R13, R14, R15, R18, R19, R20, and R21 are individually a $C_1$–$C_{20}$ straight chain aliphatic radical, [$C_1$] *a* $C_3$–$C_{20}$ branched chain [alipahtic] *aliphatic* radical, [or] *a* $C_3$–$C_{10}$ cyclic aliphatic [radicla] *radical*, [or $C_3$] *a* $C_6$–$C_{10}$ aromatic radical, or a heterocyclic radical selected from the group consisting of 1-methyl-1,4-dihydronicotinoyl, [piperidinyl, pyridinyl, furanyl, thiophenyl] *piperidyl, pyridyl, furyl, thienyl*, and pyrazinyl with the provisos that (1) R10, R11, and R12 may also individually be an amide

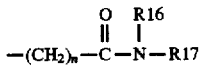

radical wherein R16 and R17 individually are a $C_1$–$C_{20}$ straight chain aliphatic radical, [$C_1$] *a* $C_3$–$C_{20}$ branched chain aliphatic radical, [or] *a* $C_3$–$C_{10}$ cyclic aliphatic radical, [or $C_3$] *a* $C_6$–$C_{10}$ aromatic radical, or a heterocyclic radical selected from the group consisting of 1-methyl-1,4-dihydronicotinoyl, [piperidinyl, pyridinyl, furanyl, thiophenyl] *piperidyl, pyridyl, furyl, thienyl*, and pyrazinyl, and n=1 to 8 and (2) R20 and R21 may also individually be [H] *hydrogen* or

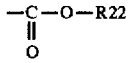

wherein R22 is [H or ] *hydrogen*, a $C_1$–$C_{20}$ straight chain aliphatic radical, [$C_1$] *a* $C_3$–$C_{20}$ branched chain aliphatic radical, [or] *a* $C_3$–$C_{10}$ cyclic aliphatic radical, [or $C_3$] *a* $C_6$–$C_{10}$ aromatic radical, or a heterocyclic radical selected from the group consisting of 1-methyl-1,4-dihydronicotinoyl, [piperidinyl, pyridinyl, furanyl, thiophenyl] *piperidyl, pyridyl, furyl, thienyl*, and pyrazinyl[, and n is an integer of 1 to 8];

R3 is selected from the group consisting of hydrogen, hydroxy, keto, [$C_1$–$C_{18}$ alkyloxy,] aryloxy, [and] amino, *and* $C_1$–$C_{18}$ *alkyloxy*; and R4, R5, and R6 individually are selected from the group consisting of [$C_1$–$C_{18}$ alkyl,] aryl, halo, [and] trifluoroalkyl, *and* $C_1$–$C_{18}$ *alkyl*;

except when [R1 is hydroxyl, R3 and] R6 [are each hydrogen,] *is halo* and R4 and R5 are each $CH_3$, then R2 is not acetyl[,2-hydroxyethanonyl, or 1-hydroxyethyl] *or 2-hydroxyethanoyl and R3* is not β-*hydroxyl*.

7. A method of treating the symptoms of premenstrual syndrome and post natal depression comprising administering to a patient in need thereof a premenstrual syndrome or post nasal depression treating effective amount of a compound of claim 6.

8. The method of claim 7 wherein said effective amount is sufficient to maintain the amount of progesterone or its metabolites in a patient to whom such dosage is given at a level substantially equivalent to the level of progesterone or its metabolites prior to the onset of menses for the treatment of premenstrual syndrome, or prior to birth for the treatment of postnatal depression.

9. A method of treating the frequency and occurrence of convulsions comprising administering to a patient in need thereof a convulsion combatting effective amount of a compound of claim 6.

10. A method of modulating the excitability of neuron activity in animals comprising administering to an animal in need thereof a neuron activity excitability modulating effective amount of a compound of claim 6.

* * * * *